(12) United States Patent
Sansoucy (10) Patent No.: US 9,878,143 B2
(45) Date of Patent: Jan. 30, 2018

(54) ANTIMICROBIAL LUER ADAPTER

(75) Inventor: Michael Sansoucy, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 1561 days.

(21) Appl. No.: 12/894,966

(22) Filed: Sep. 30, 2010

(65) Prior Publication Data

US 2012/0083750 A1   Apr. 5, 2012

(51) Int. Cl.
| | |
|---|---|
| A61M 25/16 | (2006.01) |
| A61M 25/18 | (2006.01) |
| A61M 39/00 | (2006.01) |
| A61M 39/10 | (2006.01) |
| A61M 5/32 | (2006.01) |
| A61M 39/16 | (2006.01) |
| A61L 29/16 | (2006.01) |
| A61M 25/00 | (2006.01) |

(52) U.S. Cl.
CPC ........... *A61M 39/162* (2013.01); *A61L 29/16* (2013.01); *A61L 2300/404* (2013.01); *A61L 2400/18* (2013.01); *A61M 25/0009* (2013.01); *A61M 25/0097* (2013.01); *A61M 2025/0056* (2013.01); *A61M 2039/1083* (2013.01)

(58) Field of Classification Search
CPC .. A61M 39/16; A61M 39/162; A61M 39/165; A61M 39/10; A61M 2025/0056; A61M 25/0017; A61M 2039/1083; A61M 25/0009; A61M 25/0097; A61L 2300/104; A61L 2300/404; A61L 2300/62; A61L 2300/606; A61L 29/145; A61L 29/146; A61L 29/148; A61L 31/148; A61L 31/145; A61L 31/146; A61L 2400/18; A61L 29/16

USPC ............... 604/265, 326, 175, 523, 533, 536; 424/403, 426, 446, 604; 264/271.1
See application file for complete search history.

(56) References Cited

U.S. PATENT DOCUMENTS

| 4,925,668 A | * | 5/1990 | Khan et al. .................... 424/422 |
| 5,026,359 A | * | 6/1991 | Burroughs .......... A61M 1/0096 |
| | | | 210/501 |
| 5,049,139 A | * | 9/1991 | Gilchrist ................ A01N 59/16 |
| | | | 604/265 |

(Continued)

FOREIGN PATENT DOCUMENTS

| WO | WO 95/21648 A1 | 8/1995 |
| WO | 0143788 A2 | 6/2001 |

(Continued)

OTHER PUBLICATIONS

Extended European Search Report corresponding to Eruopean Application No. EP 11 18 3050.1; completed on Jan. 9, 2012; dated Jan. 16, 2012; 5 Pages.

(Continued)

*Primary Examiner* — Jason Flick (57) ABSTRACT

A luer adapter includes a body including an inner surface defining a lumen and first and second ends. Each end is adapted to connect to a medical device. An antimicrobial material is positioned at least on a portion of the inner surface. A barrier is positioned between the lumen and the antimicrobial material and permits the passage of the antimicrobial material therethrough upon exposure to moisture. The barrier may include hydrophilic material.

33 Claims, 7 Drawing Sheets

(56) References Cited

U.S. PATENT DOCUMENTS

| | | | |
|---|---|---|---|
| 5,423,773 A * | 6/1995 | Jimenez | A61M 25/0012 604/526 |
| 5,443,454 A * | 8/1995 | Tanabe | A61B 17/12022 604/264 |
| 5,470,585 A | 11/1995 | Gilchrist | |
| 5,972,371 A | 10/1999 | Gilchrist et al. | |
| 6,143,318 A | 11/2000 | Gilchrist et al. | |
| 6,187,290 B1 | 2/2001 | Gilchrist et al. | |
| 6,447,805 B1 | 9/2002 | Healy | |
| 6,528,443 B1 | 3/2003 | Healy | |
| 6,555,491 B1 | 4/2003 | Healy | |
| 6,605,751 B1 | 8/2003 | Gibbins et al. | |
| 7,531,005 B1 | 5/2009 | Healy et al. | |
| 8,137,735 B2 | 3/2012 | Wang et al. | |
| 8,203,029 B2 * | 6/2012 | Gibbins et al. | 602/48 |
| 2002/0068093 A1 * | 6/2002 | Trogolo | A61L 27/306 424/618 |
| 2004/0116551 A1 | 6/2004 | Terry | |
| 2005/0159704 A1 * | 7/2005 | Scott et al. | 604/103.02 |
| 2006/0193894 A1 | 8/2006 | Jen et al. | |
| 2007/0078413 A1 * | 4/2007 | Stenzel | A61L 31/08 604/265 |
| 2008/0051911 A1 * | 2/2008 | Rucker | A61F 2/04 623/23.7 |
| 2010/0034882 A1 * | 2/2010 | Gibbins | A61K 9/70 424/486 |

FOREIGN PATENT DOCUMENTS

| | | |
|---|---|---|
| WO | 2005011799 A1 | 2/2005 |
| WO | WO 2006/093725 A1 | 9/2006 |
| WO | WO 2008/014448 A2 | 1/2008 |

OTHER PUBLICATIONS

V Link Brochure—V Link with VitalShield Protective Coating; Luer Activated Device, Enhanced Efficacy; The First antimicrobial I V connector; Baxter; 2 pages.

Japanese Office Action dated Jan. 22, 2013 from Japanese Application No. 2011-217297.

Canadian Office Action dated Jan. 11, 2013 from Canadian Application No. 2,753,574.

Examination Report from Counterpart European Patent Application No. 13170645.9, dated Oct. 22, 2014, 4 pp.

* cited by examiner

ANTIMICROBIAL LUER ADAPTER

BACKGROUND

Technical Field

The present disclosure generally relates to luer adapters. More particularly, the present disclosure relates to an antimicrobial luer adapter for use with a medical device.

Description of the Related Art

Luer adapters are standard fittings used on medical devices. A luer adapter, or luer fitting, it often used to connect and disconnect the medical tubing of one medical device to the medical tubing of another medical device, or to enable the connection of a syringe to a medical device to sample the fluid therein. Luer adapters provide quick connect and disconnect capabilities, with a substantially water tight seal when properly connected.

For example, luer adapters are often used on catheter assemblies. Catheters are flexible medical instruments which facilitate the withdrawal and introduction of fluids from and to body cavities, ducts, and vessels. Catheters have particular application in a hemodialysis procedure where blood is withdrawn from a blood vessel for treatment, and subsequently returned to the blood vessel for circulation. Known hemodialysis catheter assemblies include multiple lumen catheters, such as dual lumen or triple-lumen catheters, which permit bi-directional fluid flow within the catheter whereby one lumen is dedicated for withdrawal of blood from a vessel and the other lumen is dedicated for return of treated blood to the vessel.

Hemodialysis catheter assemblies also often include a hub assembly and extension tubes. The hub assembly connects the catheter to the extension tubes, which connect the hub assembly and catheter to a hemodialysis machine. During an exemplary hemodialysis procedure, a multiple lumen catheter is inserted into a body and blood is withdrawn through an arterial lumen of the catheter. The removed blood is directed to a hemodialysis machine, via a hub assembly and an extension tube, which dialyzes, or purifies, the blood to remove waste and toxins. The dialyzed blood is returned to the patient through a venous lumen of the catheter via the hub assembly and a second extension tube.

A luer adapter is used for connecting each extension tube to a mating tube on a hemodialysis machine. Thus, luer adapters must be durable and robust to resist breaking or cracking during repeated connection and disconnection to and from a hemodialysis machine. The repeated connection and disconnection of a medical device which is placed in a patient's body may expose the patient to infections. For example, as a dialysis technician handles the luer adapter to connect and disconnect the patient from the hemodialysis machine, microbes may be deposited on and into the luer adapter. These microbes may then produce intra-lumenal and extra-lumenal microbial colonization, which can then propagate down the catheters intra-lumenal surfaces, or can be carried into the body through the fluid within the luer adapter connected to the extension tube. Thus, it is also desirable that the luer adapter have anti-microbial characteristics. As such, it is known to mix anti-microbials into the material used to form the luer adapter. However, such anti-microbials mixed into the material used to make the luer adapter tends to weaken the strength and/or robustness of the luer adapter.

Consequently, there is a continuing need for a luer adapter which includes anti-microbial characteristics while maintaining its durability and robustness.

SUMMARY

According to one aspect of the present disclosure, a luer adapter includes a body having an inner surface defining a lumen, and first and second ends. Each end is adapted to connect to a medical device. The body supports an antimicrobial material positioned on at least a portion of the inner surface. The antimicrobial material may define a layer positioned on the inner surface. A barrier is positioned between the lumen and the antimicrobial material and permits the passage of the antimicrobial material therethrough upon exposure to moisture. The barrier may include hydrophilic material. The hydrophilic material may define a second innermost layer.

One or both of the hydrophilic material and the antimicrobial material may define a mounting surface. In embodiments, the mounting surface has one or more ribs positioned thereon to secure the hydrophilic material and the antimicrobial material to one another. In embodiments, one or both of the hydrophilic material and the antimicrobial material may include a roughened surfaced that facilitates the securement of the hydrophilic material and the antimicrobial material relative to one another.

The antimicrobial material may include one or more of silver, copper, and zinc. The hydrophilic material may be made from biodegradable materials selected from the group including synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. The hydrophilic material may be made from non-biodegradable materials selected from the group including polyolefins, polyolefin blends, polyolefin copolymers, polyethylene, polydimethylsiloxane, polypropylene, ultra high molecular weight polyethylene, polyamides, polyesters, polyethylene terephthalate, polytetrafluoroethylene, polyethers, polyetherimides, polyether-esters, polybutester, polytetramethylene ether glycol, 1,4-butanediol, polyurethanes, styrenics, polycarbonates, vinyls, and combinations thereof.

In embodiments, the antimicrobial material may include one or more zeolite materials. The zeolite material may be naturally occurring or synthetic zeolite.

According to another aspect of the disclosure, a luer adapter includes a body including an inner surface defining a lumen, an outer surface, and first and second ends. Each end is adapted to connect to a medical device. The body supports an antimicrobial element positioned on at least one of the inner and outer surface in the form of one or more antimicrobial elements. The body defines one or more recesses for receiving the antimicrobial element. The antimicrobial element may include ions selected from the group comprising silver, copper, and zinc. The antimicrobial element may include antimicrobial glass. The antimicrobial element may dissolve in the presence of moisture. The one or more antimicrobial elements may include the antimicrobial material.

One or both of the inner surface and the outer surface may include a barrier positioned adjacent the antimicrobial element. The antimicrobial material of the antimicrobial element is able to pass through the barrier upon exposure to moisture. The barrier may include hydrophilic material. The hydrophilic material covers the one or more recesses to enclose the antimicrobial material. The antimicrobial element may be annular in shape.

The hydrophilic material may be radially adjacent the one or more antimicrobial elements with respect to a longitudinal axis of the body. The hydrophilic material may permit moisture to pass therethrough in order to enable the antimicrobial material to dissolve. The hydrophilic material may permit the ions to elute along one or both of the inner and outer surfaces. The hydrophilic material may include polymeric material.

According to another aspect of the present disclosure, a method of manufacturing a medical device includes the steps of providing a mold of a body portion of a luer adapter; providing one or more extrusions including an antimicrobial material; positioning the one or more extrusions on a core-pin of the mold; and forming the body portion of the luer adapter via injection molding about the one or more extrusions such that the one or more extrusions and the body portion are formed in a unitary structure, wherein in the unitary structure defines a luer adapter. The extrusion may also include a hydrophilic material. The method may include coextruding each of the antimicrobial material and the hydrophilic material.

BRIEF DESCRIPTION OF THE DRAWINGS

Various embodiments of the presently disclosed luer adapters are described herein with references to the accompanying drawings, wherein.

DETAILED DESCRIPTION OF THE EMBODIMENTS

In the discussion that follows, the term "proximal" or "trailing" will refer to the portion of a structure that is closer to a clinician, while the term "distal" or "leading" will refer to the portion of a structure that is farther from the clinician. As used herein, the term "subject" refers to a human patient or other animal. The term "clinician" refers to a doctor, nurse or other care provider and may include support personnel. The term "biodegradable" as used herein refers to materials which decompose, or lose structural integrity under body conditions (e.g. enzymatic degradation or hydrolysis).

Figure 1:
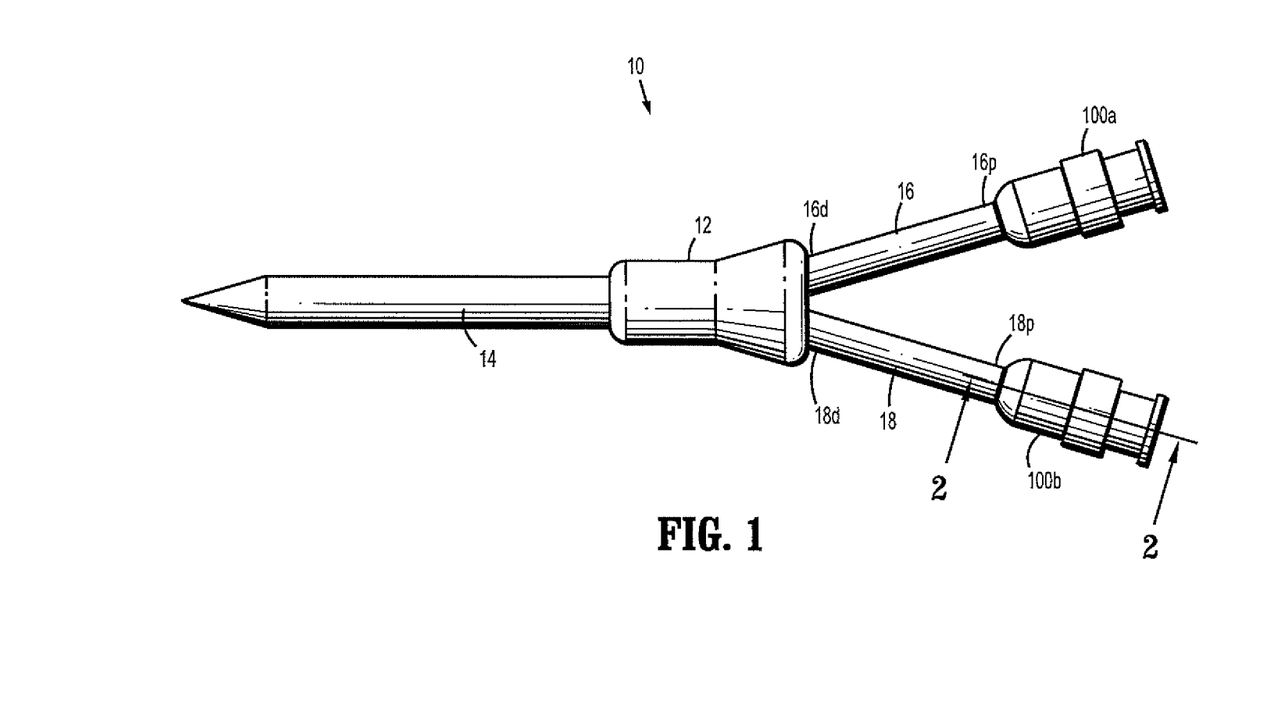
FIG. 1 is a side view of a catheter assembly including a luer adapter in accordance with the present disclosure.

Referring to FIG. 1, which illustrates an exemplary use of a luer adapter of the present invention, a catheter assembly 10 which includes a hub assembly 12, a catheter 14 extending distally from the hub assembly 12, and first and second extension tubes 16, 18 extending proximally from the hub assembly 12. Hub assembly 12 fluidly couples first and second extension tubes 16, 18 to catheter 14. The first extension tube 16 has a proximal end 16p and a distal end 16d. Distal end 16d of first extension tube 16 is attached to hub assembly 12 and proximal end 16p of first extension tube 16 is connected to a first luer adapter 100a. Second extension tube 18 has a proximal end 18p and a distal end 18d. Distal end 18d of second extension tube 18 is coupled to hub assembly 12, while proximal end 18p of second extension tube 18 is coupled to a second luer adapter 100b.

Figure 2:
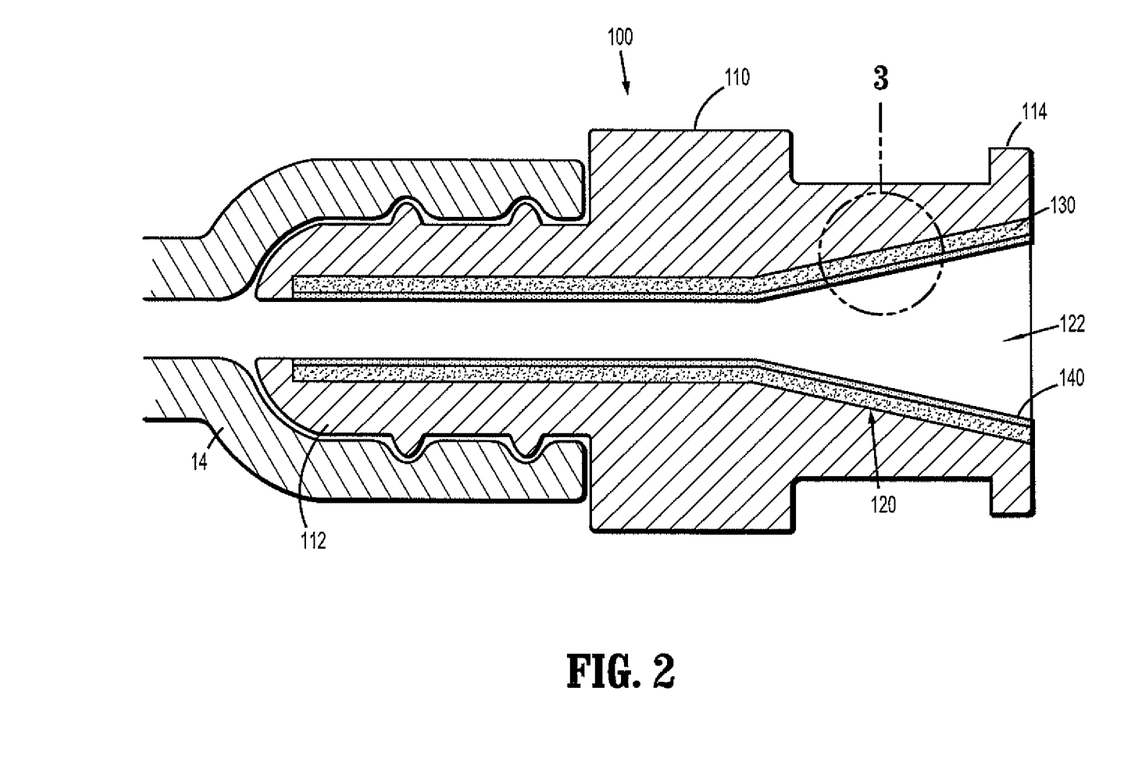
FIG. 2 is an enlarged cross-sectional view of the luer adapter of the catheter assembly shown in FIG. 1 taken along section lines 2-2.
Figure 3:
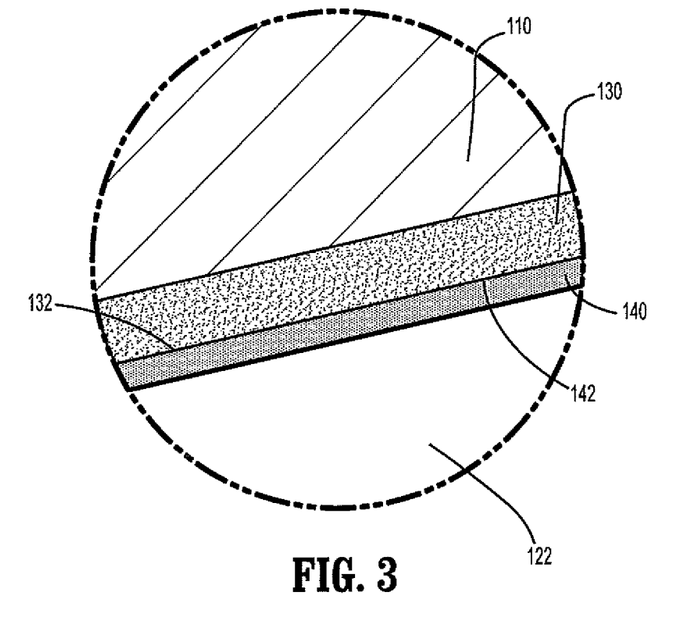
FIG. 3 is an enlarged cross-sectional view of the indicated area of detail shown in FIG. 2, the indicated area of detail illustrating a portion of one embodiment of an inner surface of the luer adapter.

As illustrated in FIG. 2, one embodiment of a luer adapter 100 includes a body 110 having first end 112 and a second end 114. Each end 112,114 is adapted to connect to a medical device. For example, the first end 112 may be secured to one of the extension tubes 16, 18 of the exemplary catheter assembly 10 and the second end 114 may be secured to a mating luer connector on a hemodialysis machine blood line or to a syringe (not shown). The body 110 has an inner surface 120 defining a lumen 122 in which an antimicrobial material 130 is supported. A barrier such as a hydrophilic material 140 may be attached to the antimicrobial material 130 such that the hydrophilic material 140 is positioned between the lumen 122 and the antimicrobial material 130. In embodiments, the hydrophilic material 140 may include any suitable anti-thrombotic material. The hydrophilic material 140 permits the passage of at least a portion of the antimicrobial material 130 therethrough upon exposure to liquid that may be present in the lumen 122. The hydrophilic material 140 may also be configured and dimensioned to prevent dissolved material from moving into the bloodstream as blood and/or other bodily fluids pass through the lumen 122. In particular, the hydrophilic material 140 may be sized and shaped to conform to national and/or international standards for allowing or inhibiting particles within the bloodstream. For example, the hydrophilic material 140 may be adapted to control the rate of elution of the dissolved material by providing a diffusion barrier that limits transport of thrombotic particles greater than a predetermined size into the bloodstream. In embodiments, the hydrophilic material 140 may be formed of a polymer, e.g. a polyurethane such as Tecophilic, which is sold by The Lubrizol Corporation.

With reference to FIGS. 3-6, the hydrophilic material 140 defines a mounting surface 142 and the antimicrobial material 130 defines a mounting surface 132 to which the mounting surface 142 of the hydrophilic material 140 attaches. The hydrophilic material 140 may be attached or bonded to the antimicrobial material 130 by either a mechanical bond or a chemical bond, or both. Examples of a chemical bond include adhesives or molecular bonds. For example, the hydrophilic material 140 may be co-extruded or overmolded with the antimicrobial material to produce a covalent bond between the polymers. Similarly, the antimicrobial material 140 may be co-extruded or overmolded onto the inner surface 120 of the body 110 to produce a covalent bond between the polymers.

Figure 4:
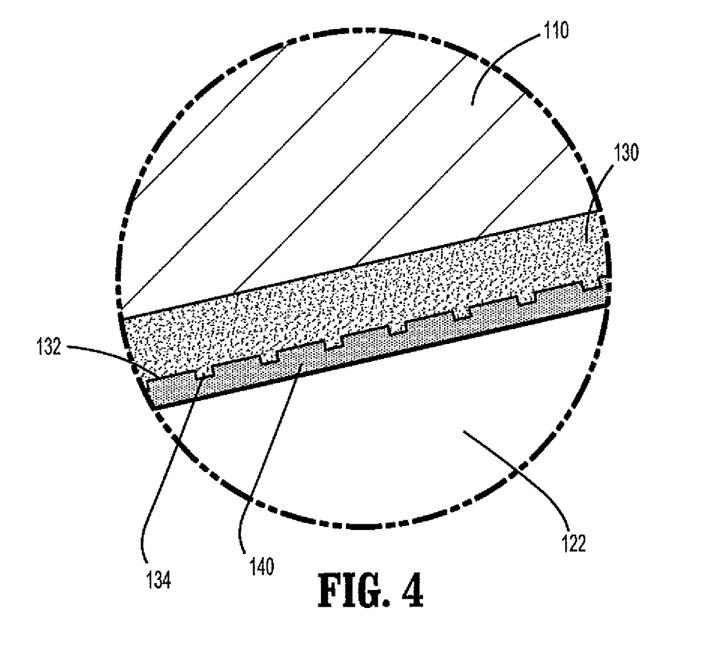
FIG. 4 is an enlarged cross-sectional view of an inner surface of an alternate embodiment of the presently disclosed luer adapter.
Figure 5:
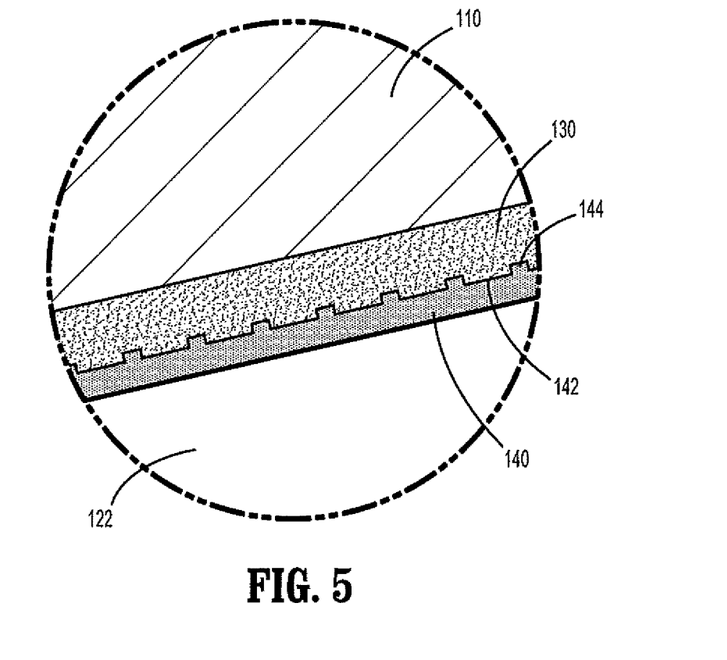
FIG. 5 is an enlarged cross-sectional view of an inner surface of another alternate embodiment of the presently disclosed luer adapter.
Figure 6:
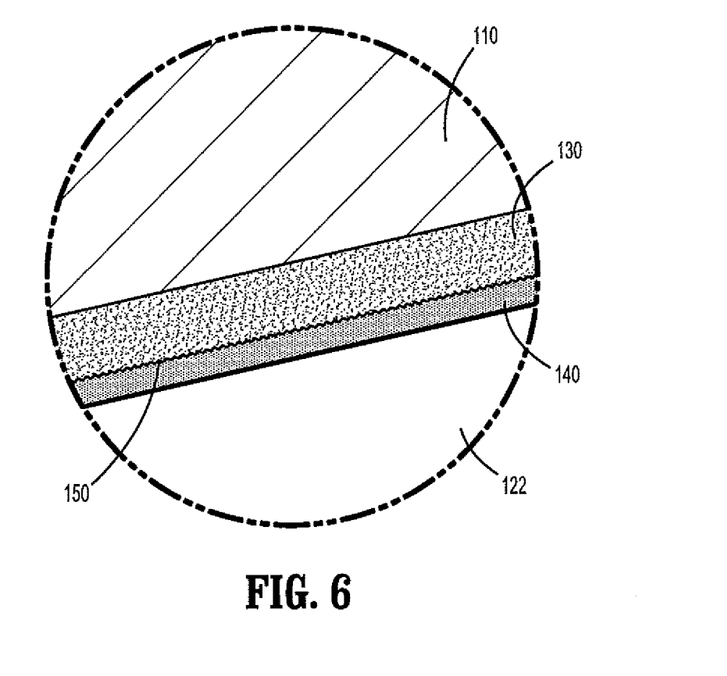
FIG. 6 is an enlarged cross-sectional view of an inner surface of yet another alternate embodiment of the presently disclosed luer adapter.

A mechanical bond may be produced between the hydrophilic material 140 and the antimicrobial material 130, as well as the antimicrobial material 130 and the inner surface 120 of the body 110, by including undercuts, ribs or a surface roughness between the layers of polymer. For example, as best shown in FIG. 4, the mounting surface 132 may have one or more ribs 134 positioned thereon to secure the hydrophilic material 140 and the antimicrobial material 130 to one another. Similarly, as best shown in FIG. 5, the mounting surface 142 may have one or more ribs 144 positioned thereon to secure the hydrophilic material 140 and the antimicrobial material 130 to one another. In other embodiments, one or both of the hydrophilic material 140 and the antimicrobial material 130 may include a roughened surfaced 150 (FIG. 6) that facilitates the securement of the hydrophilic material 140 and the antimicrobial material 130 relative to one another.

The antimicrobial material 130 may be employed in single and/or multiple layers and/or compositions. The antimicrobial material 130 may include dissolving material that can dissolve, such as, for example, the antimicrobial material described in U.S. Pat. No. 6,143,318 and produced by Mo-Sci Corporation. The antimicrobial material 130 may include one or more of silver, copper, and zinc. In embodiments, any suitable anti-microbial that uses water to transport media, for example, silver, may be appropriate. In embodiments, any suitable anti-biotic or anti-septic may also be appropriate, such as silver impregnated zeolites, silver sulphadiazene, quaternary ammonium compounds, silver and silver compounds, iodine and iodine compounds, sodium hypochloride, sodium bicarbonate, and triclosan.

Similarly, the hydrophilic material 140 may be employed in single and/or multiple layers and/or compositions. The hydrophilic material 140 may be made from biodegradable materials selected from the group including synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. The hydrophilic material 140 may be made from non-biodegradable materials selected from the group including polyolefins and polyolefin blends and/or copolymers, polyethylene, polydimethylsiloxane, polypropylene, ultra high molecular weight polyethylene, polyamides, polyesters, polyethylene terephthalate, polytetrafluoroethylene, polyethers, polyetherimides, polyether-esters, polybutester, polytetramethylene ether glycol, 1,4-butanediol, polyurethanes, styrenics, polycarbonates, vinyls, as well blends and copolymers containing at least one of the previous disclosed polymers and any other suitable polymers.

Figure 7:
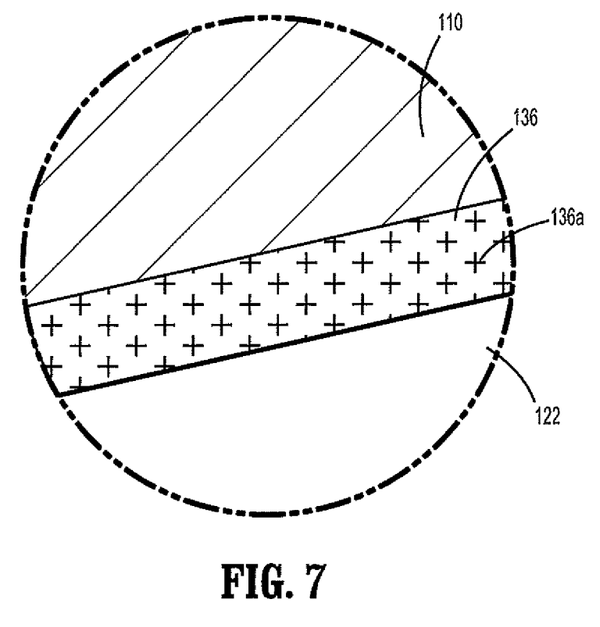
FIG. 7 is an enlarged cross-sectional view of an inner surface of another alternate embodiment of the presently disclosed luer adapter.

In embodiments, the antimicrobial material 130 may include non-dissolving material. For example, the antimicrobial material 130 may include one or more zeolite materials 136 (FIG. 7), including any commercially available zeolite materials. The zeolite material 136 may be naturally occurring or synthetic zeolites. The zeolite material may be positioned adjacent a barrier such as a hydrophilic material to inhibit thrombotic diffusion of the zeolite material into the bloodstream, as discussed above. As illustrated in FIG. 7, the zeolite material 136 may include ions 136*a* selected from the group including silver, copper, zinc, as well as other antiseptics.

Figure 8:
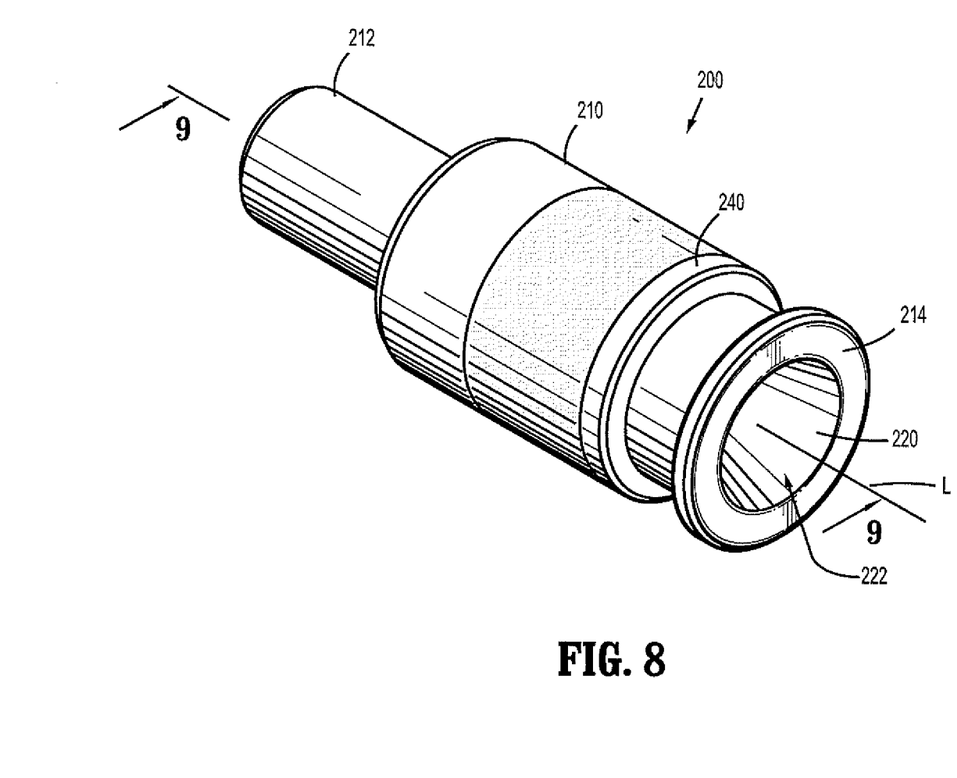
FIG. 8 is a perspective view of another embodiment of a luer adapter in accordance with the present disclosure.
Figure 9:
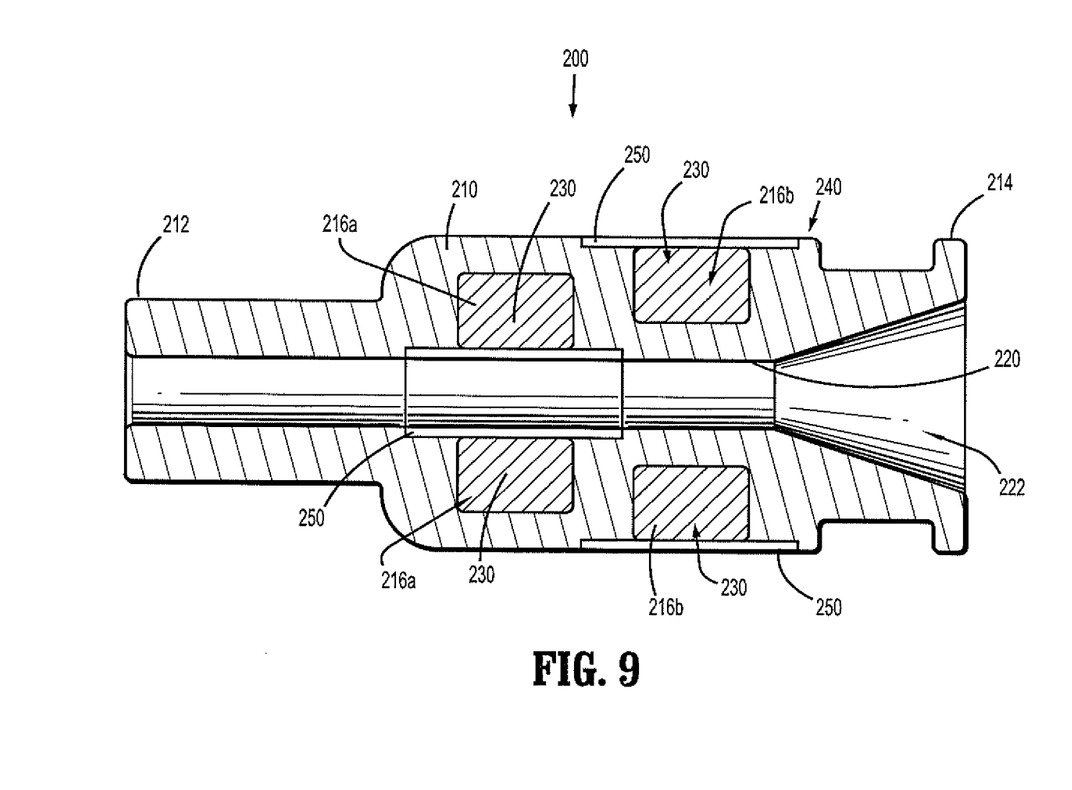
FIG. 9 is a cross-sectional view taken along section line 9-9 of FIG. 8.

As illustrated in FIGS. 8-9, another embodiment of a luer adapter is generally referred to as 200 and is similar to luer adapter 100. Lluer adapter 200 includes a body 210 including first and second ends 212, 214, an inner surface 220 and an outer surface 240. The inner surface 220 defines a lumen 222. The body 210 supports one or more antimicrobial elements 216 extending therethrough which include an antimicrobial material 230. While antimicrobial elements 216 are described and shown as annular elements, the elements 216 may be any suitable shape. In use, the one or more antimicrobial elements 216 may comprise any suitable antimicrobial glass, such as the material disclosed above produced by Mo-Sci Corporation, or hydrophilic material including antiseptic zeolites, or any other suitable antimicrobial and/or antiseptic. Alternately, other types of antimicrobials may be used with the luer adapter 200. A first annular element 216*a* may be positioned adjacent the inner surface 220 of the body 210. A second annular element 216*l*) may be positioned adjacent the outer surface 240 of the body 210.

One or both of the inner surface 220 and the outer surface 240 may include a barrier, such as a hydrophilic material 250, positioned adjacent the antimicrobial material 230. As described above, the antimicrobial material 230 is able to pass through the hydrophilic material 250 upon exposure to liquid or moisture. The hydrophilic material 250 may be tailored to control the release of the antimicrobial material 230. For example, the thickness or hydrophilicity of hydrophilic material 250 may be altered to provide more or less release of the antimicrobial material 230. The antimicrobial material 230 may include ions (not shown) selected from the group including silver, copper, and zinc.

In embodiments, the antimicrobial glass, discussed above, may elute ions, such as silver ions. The elution of the ions from the antimicrobial glass is particularly beneficial when the catheter assembly 10 is locked with a lock-solution, such as hepranized saline which is commonly used. This elution ensures that microbes do not colonize along one or both the inner surface 220 and/or the outer surface 240 of the body 210. For example, the outer surface 240 of the body 210 may be wetted when cleaned prior to and after dialysis sessions, which may released silver ions during this procedure to reduce the microbial colonization on the outer surface 240. The antimicrobial material 230 may be released by dissolving in the presence of moisture. The one or more antimicrobial elements 216 may be made of the antimicrobial material or may include the antimicrobial material 230 therein, or the antimicrobial material 230 may be positioned on the one or more antimicrobial elements 216 as a coating or layer.

The hydrophilic material 250 may be radially adjacent the one or more antimicrobial elements 216 with respect to a longitudinal axis "L" (FIG. 8) of the body 210. The hydrophilic material 250 may permit moisture to pass therethrough in order to enable the antimicrobial material 230 to dissolve and be released. The hydrophilic material 250 may permit the ions to elute along one or both of the inner and outer surfaces 220, 240. The hydrophilic material 250 may include polymeric materials, blends and/or materials including at least a part thereof.

According to one aspect, a method of manufacturing a medical device includes the step of providing a mold of a body portion of a luer adapter. One step includes providing one or more extrusions including an antimicrobial material and/or a hydrophilic material. The extrusion may be of any shape, including those shapes described above of the antimicrobial material and hydrophilic material. The method may include coextruding the antimicrobial material and/or the hydrophilic material into any shape. The method involves positioning the one or more extrusions on a core-pin of the mold. The body portion of the luer adapter may be formed via injection molding about the one or more extrusions such that the one or more extrusions and the body portion are formed into essentially a unitary body defining a luer adapter wherein the antimicrobial material is assembled with, not mixed in, the body portion.

Suitable non-biodegradable materials which may be used to construct the body 110 of the present disclosure include polyethers, polyetherimides, polycarbonates, polyurethanes, fluorinated polymers (e.g., fluoroethylenes, propylenes, fluoroPEGs), polyolefins such as polyethylene, poly ethylene terepththalate (PET), nylons, polyamides, vinyls, styrenics, ultra high molecular weight polyethylene (UHM-WPE), polybutesters, polyaryletherketone, copolymers, blends and combinations thereof.

Suitable materials of the present disclosure can be processed within the purview of those skilled in the art including, but not limited to extrusion, co-extrusion, injection molding, compression molding, overmolding, as well as machining.

Optionally, the luer adapter may include other coatings on its interior and/or exterior to enhance the surface properties in clinically relevant manners. As used herein, the term "coating" is not limited to liquids and may also include solids. Coatings can be applied using any method within the purview of those skilled in the art. For example, hydrophilic material 140 may be applied as a brush or dip coating. More specifically, for example, polyurethane may be dissolved in tetrahydrofuran (THF) and dip coated onto the body 110.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A luer adapter, comprising:
   a body including an inner surface defining a lumen, and first and second ends, each end being adapted to connect to a medical device;
   an antimicrobial material positioned on at least a portion of the inner surface; and
   a barrier positioned between the lumen and the antimicrobial material, the barrier being bonded to the antimicrobial material, the antimicrobial material defining mounting structures with which the antimicrobial material and the barrier are constrained together, wherein the barrier permits the passage of the antimicrobial material therethrough upon exposure to moisture.

2. The luer adapter according to claim 1, wherein the barrier includes a hydrophilic material.

3. The luer adapter according to claim 2, wherein the antimicrobial material defines a layer positioned on the inner surface and the hydrophilic material defines a second innermost layer.

4. The luer adapter according to claim 2, wherein the mounting structures include at least one rib.

5. The luer adapter according to claim 2, wherein the mounting surface includes a roughened surface.

6. The luer adapter according to claim 2, wherein the hydrophilic material includes biodegradable materials selected from the group comprising synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof.

7. The luer adapter according to claim 2, wherein the hydrophilic material includes non-biodegradable materials selected from the group comprising polyolefins, polyolefin blends, polyolefin copolymers, polyethylene, polydimethylsiloxane, polypropylene, ultra high molecular weight polyethylene, polyamides, polyesters, polyethylene terephthalate, polytetrafluoroethylene, polyethers, polyetherimides, polyether-esters, polybutester, polytetramethylene ether glycol, 1,4-butanediol, polyurethanes, styrenics, polycarbonates, vinyls, and combinations thereof.

8. The luer adapter according to claim 1, wherein the antimicrobial material is selected from the group comprising silver, copper, and zinc.

9. The luer adapter according to claim 1, wherein the antimicrobial material includes at least one zeolite material.

10. The luer adapter according to claim 9, wherein the zeolite material is naturally occurring zeolite.

11. The luer adapter according to claim 9, wherein the zeolite material is synthetic zeolite.

12. The luer adapter according to claim 11, wherein the zeolite material includes ions selected from the group comprising silver, copper, and zinc.

13. A luer adapter, comprising:
    a body including an inner surface defining a lumen, an outer surface, and first and second ends, each end being adapted to connect to a medical device;
    an antimicrobial material positioned on at least one of the inner surface or the outer surface, the antimicrobial material comprising a polymer; and
    a barrier positioned adjacent the antimicrobial material, the barrier being bonded to the polymer of the antimicrobial material, wherein the antimicrobial material is able to pass through the barrier upon exposure to moisture.

14. The luer adapter according to claim 13, wherein the barrier includes a hydrophilic material.

15. The luer adapter according to claim 14, wherein the hydrophilic material is radially adjacent the antimicrobial material with respect to a longitudinal axis of the body.

16. The luer adapter according to claim 14, wherein the antimicrobial material comprises at least one antimicrobial element configured to dissolve in the presence of moisture.

17. The luer adapter according to claim 16, wherein the hydrophilic material permits moisture to pass therethrough to enable the at least one antimicrobial element to dissolve.

18. The luer adapter according to claim 14, wherein the antimicrobial material includes ions selected from the group consisting of silver, copper, and zinc.

19. The luer adapter according to claim 18, wherein the hydrophilic material permits the ions to elute along the at least one of the inner surface or the outer surface.

20. The luer adapter according to claim 14, wherein the hydrophilic material includes polymeric material.

21. The luer adapter according to claim 14, wherein the body defines at least one annular recess for receiving the antimicrobial material.

22. The luer adapter according to claim 21, wherein the hydrophilic material covers the at least one annular recess to enclose the antimicrobial material.

23. The luer adapter according to claim 13, wherein the antimicrobial material defines an annular.

24. The luer adapter according to claim 13, wherein the antimicrobial material includes antimicrobial glass.

25. The luer adapter according to claim 1, wherein the barrier is mechanically bonded to the antimicrobial material.

26. The luer adapter according to claim 25, wherein the mounting structures comprise an undercut, a rib, or a surface roughness.

27. The luer adapter according to claim 1, wherein the barrier is chemically bonded to the antimicrobial material.

28. The luer adapter according to claim 27, wherein the chemical bond comprises an adhesive bond between the barrier and the antimicrobial material.

29. The luer adapter according to claim 13, wherein the barrier is mechanically bonded to the polymer of the antimicrobial material.

30. The luer adapter according to claim 13, wherein the barrier comprises a polymer that is chemically bonded to the polymer of the antimicrobial material.

31. The luer adapter according to claim 13, wherein the barrier comprises a polymer that is covalently bonded to the polymer of the antimicrobial material.

32. The luer adapter according to claim 13, wherein at least one of the barrier or the antimicrobial material defines a mounting surface including mounting structures with which the barrier is bonded to the polymer of the antimicrobial material.

33. The luer adapter according to claim 27, wherein the chemical bond comprises a molecular bond between the barrier and the antimicrobial material.

* * * * *

UNITED STATES PATENT AND TRADEMARK OFFICE
CERTIFICATE OF CORRECTION

PATENT NO. : 9,878,143 B2  
APPLICATION NO. : 12/894966  
DATED : January 30, 2018  
INVENTOR(S) : Michael R. Sansoucy Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1573 days.

Signed and Sealed this  
Nineteenth Day of June, 2018

Andrei Iancu  
*Director of the United States Patent and Trademark Office*